(12) United States Patent
Rai et al.

(10) Patent No.: US 8,298,440 B2
(45) Date of Patent: Oct. 30, 2012

(54) METHODS AND COMPOSITIONS FOR INHIBITING VINYL AROMATIC MONOMER POLYMERIZATION

(75) Inventors: Vinod Kumar Rai, Karnataka (IN); Sherif Eldin, Bellaire, TX (US); Mary King, Kingwood, TX (US); John Link, Humble, TX (US); Alagarsamy A. Subbiah, Karnataka (IN); H. Kelly Herrington, Thicket, TX (US)

(73) Assignee: General Electric Company, Schenectady, NY (US)

( * ) Notice: Subject to any disclaimer, the term of this patent is extended or adjusted under 35 U.S.C. 154(b) by 138 days.

(21) Appl. No.: 12/793,226

(22) Filed: Jun. 3, 2010

(65) Prior Publication Data

US 2011/0297878 A1    Dec. 8, 2011

(51) Int. Cl.
*C09K 15/08* (2006.01)
(52) U.S. Cl. .................. 252/182.29; 585/5; 585/952
(58) Field of Classification Search .............. 585/3, 952; 252/182.29; 525/3, 5, 952
See application file for complete search history.

(56) References Cited

U.S. PATENT DOCUMENTS

| | | | |
|---|---|---|---|
| 4,032,547 A | 6/1977 | Bacha et al. | |
| 4,040,911 A * | 8/1977 | Bacha et al. | 203/9 |
| 4,929,778 A | 5/1990 | Roling | |
| 5,470,440 A | 11/1995 | Arhancet | |
| 5,562,863 A | 10/1996 | Arhancet | |
| 5,616,774 A * | 4/1997 | Evans et al. | 252/182.18 |
| 6,024,894 A | 2/2000 | Arhancet | |
| 6,926,820 B2 | 8/2005 | Eldin et al. | |
| 7,128,826 B2 | 10/2006 | Eldin et al. | |
| 2003/0065177 A1 * | 4/2003 | Sheridan et al. | 544/170 |

FOREIGN PATENT DOCUMENTS

JP   2010-066553   *   3/2010

OTHER PUBLICATIONS

Hamaguchi et al., electronic translation of the specifcation of JP 2010-066553, Mar. 2010.*

* cited by examiner

*Primary Examiner* — Jeffrey Mullis
(74) *Attorney, Agent, or Firm* — Wegman, Hessler & Vanderburg

(57) ABSTRACT

Methods and compositions are provided for inhibiting the polymerization of a vinyl aromatic monomer, such as styrene monomer, during elevated temperature processing thereof or during storage or shipment of polymer containing product. The compositions comprise a combination of a quinone methide derivative A) and a phenol compound B). The methods comprise adding from about 1-10,000 ppm of the combination to the monomer containing medium, per one million parts of the monomer.

16 Claims, No Drawings

METHODS AND COMPOSITIONS FOR INHIBITING VINYL AROMATIC MONOMER POLYMERIZATION

FIELD OF THE INVENTION

The invention pertains to methods and compositions for inhibiting the undesired polymerization of vinyl aromatic monomers, such as styrene monomer, during processes such as monomer preparation, and purification, and during storage and shipment of products containing such monomers.

BACKGROUND OF THE INVENTION

Polystyrene is a thermoplastic with many desirable characteristics. It is clear, transparent, readily colored and easily fabricated. The family of styrene polymers includes polystyrene itself, copolymers of styrene with other vinyl monomers, polymers of derivatives of styrene and mixtures of polystyrene and styrene-containing copolymers with elastomers.

ABS (acrylonitrile, butadiene-styrene) resins have enjoyed tremendous commercial popularity for many years as durable, temperature and solvent resistant elastomers. On the other hand, styrene plastics are commonly used for packaging, including foams and films, coatings, in appliance fabrication, for housewares and toys, lighting fixtures and in construction materials.

It is well known that styrene monomer readily polymerizes when heated or exposed to light. Heat polymerization is rapid. In fact, polymerization increases with increasing temperature. This polymerization is undesirable during many stages of the manufacturing, processing, handling, storage and use of styrene monomers.

Common industrial methods for producing styrene include a variety of purification processes, including distillation, to remove impurities. Unfortunately, purification operations carried out at elevated temperatures result in an increased rate of undesired polymerization. Polymerization, such as thermal polymerization, during the monomer purification process, results not only in loss of desired monomer end-product, but also in loss of production efficiency caused by polymer formation or agglomeration on process equipment. In heat requiring operations, such agglomeration adversely affects heat transfer efficiency.

SUMMARY OF THE INVENTION

In accordance with aspect of the invention, a method is provided for inhibiting the polymerization of a vinyl aromatic monomer such as styrene monomer, i.e., ethylbenzene. The method comprises adding an effective polymerization inhibiting amount of a combined treatment to the monomer medium. The combined treatment comprises (A) a quinone methide derivative and (B) a phenol compound. From about 1-10,000 ppm of (A) and (B) collectively is brought into contact with the requisite vinyl aromatic monomer based on 1 million parts of the monomer. The method may, in other aspects of the invention, comprise the step of heating the monomer and, in another aspect of the invention, the monomer may be distilled to remove impurities therefrom.

In another aspect of the invention, a vinyl aromatic monomer anti-polymerization composition is provided which comprises a liquid carrier and dissolved or dispersed therein (A) a quinone methide derivative and (B) a phenol compound.

In another embodiment, the quinone methide derivative is 2,6-di-tert-butyl-4-benzylidene-cyclohexa-2,5-dienone.

In another aspect of the invention, the phenol compound (B) is 2,6-di-t-butylphenol.

In another exemplary embodiment, a liquid carrier such as a non-polar organic solvent is provided with the combined treatment (A) and (B) dissolved or dispersed therein.

DETAILED DESCRIPTION OF EXEMPLARY EMBODIMENTS

In accordance with the invention, both a quinone methide derivative A) and a phenol compound B) are conjointly utilized to inhibit polymerization of a vinyl aromatic monomer such as styrene.

The quinone methide derivatives generally have the formula:

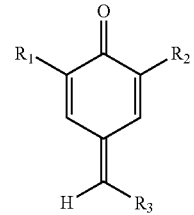

wherein:

$R_1$ and $R_2$ are independently H, $C_4$ to $C_{18}$ alkyl; $C_5$ to $C_{12}$ cycloalkyl; or $C_7$ to $C_{15}$ phenylalkyl.

Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred.

$R_3$ is preferably aryl, or aryl substituted with $C_1$ to $C_6$ alkyl, alkoxy, hydroxy, nitro, amino, carboxy, or mixtures thereof.

Means for preparing these compounds may be found in U.S. Pat. No. 4,032,547, the contents of which are wholly incorporated by reference to herein.

Preferably, the quinone methide derivative is 2,6-di-tert-butyl-4-benzylidene-cyclohexa-2,5-dienone.

The phenol compounds B) that may be utilized generally have the formula:

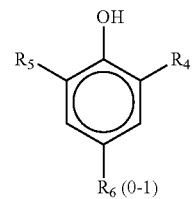

wherein $R_4$ and $R_5$ may be the same or different and are chosen from $C_1$-$C_{20}$ alkyl, $C_1$-$C_{30}$ alkaryl and substituted $C_1$-$C_{30}$ alkaryl, $R_6$, when present, is selected from $C_1$-$C_{20}$ alkyl, thiophenol, substituted thiophenol, $C_1$-$C_{40}$ alkanoic acid ester, $C_1$-$C_{30}$ alkaryl, substituted $C_1$-$C_{30}$ alkaryl, $C_1$-$C_6$ alkylamino, $C_1$-$C_6$ alkoxy, amine, polynuclear aryl and substituted polynuclear aryl.

At present, the preferred phenol B) compound is 2,6-di-t-butylphenol. Exemplary phenols include 2,6-dipropylphenol, 2,6-diethylphenol and 2,6-dimethylphenol. Also mentioned as exemplary are the hindered phenols in accord with the above formula wherein $R_4$, $R_5$ and $R_6$ are all present. These include:

2,6-di-t-butyl-4-methylphenol
4,4'-thiobis-(6-t-butyl-2-methylphenol)
octadecyl 3-(3',5'-di-t-butyl-4'-hydroxyphenyl)propionate
4,4'-methylenebis(2,6-di-t-butylphenol)
1,3,5-trimethyl-2,4,6-tris(3,5-di-t-butyl-4-hydroxybenzyl) benzene
2,6-di-t-butyl-α-dimethylamino-p-cresol
2,6-di-t-butyl-4-secbutylphenol
2,2'-methylenebis(4-ethyl-6-t-butylphenol)
2,2'-methylenebis(4-methyl-6-t-butylphenol)
2,2'-methylenebis(6-(1-methylcyclohexyl)-p-cresol; and
2,2'-methylenebis(4-methyl-6-cyclohexylphenol)

The compositions of the present invention are effective at inhibiting polymerization of vinyl aromatic monomers under processing conditions. These processing conditions include but are not limited to preparation, purification, distillation and vacuum distillation processes.

Styrene, for example, is typically processed at temperatures between 95° and 125° C. The compositions of the present invention are effective at inhibiting the polymerization of styrene over this range of temperatures.

The vinyl aromatic monomers that are treated by the compositions of the present invention include but are not limited to styrene, bromostyrene, divinylbenzene, and α-methylstyrene. The compositions of the present invention are particularly efficacious at inhibiting the polymerization of styrene monomer.

The total amount of quinone methide derivative A) and phenolic compound B) used in the methods of the present invention is that amount which is sufficient to inhibit polymerization of vinyl aromatic monomers. This amount will vary according to the conditions under which the vinyl aromatic monomer is being processed, contaminants in the system and the temperature of the system. At higher processing temperatures and higher monomer contamination, larger amounts of the inhibiting composition are required.

For purposes of the present invention, the term "effective inhibiting amount" is that amount which is effective at inhibiting vinyl aromatic monomer polymerization. Preferably, this amount ranges from about 1 part to about 10,000 parts of quinone methide derivative and phenolic compound, collectively, per 1 million parts of monomer. Most preferably, this amount will range from about 1 to 1,000 parts per million parts monomer.

Accordingly, it is possible to produce a more effective vinyl aromatic monomer polymerization inhibiting treatment than is obtained by the use of either compound by itself when measured at comparable treatment levels. This synergism or enhanced activity between components allows for the concentration of each of the components to be lowered and the total quantity of polymerization inhibitor required, particularly at higher temperatures, may be lowered while achieving a commensurate level of polymerization inhibition.

As such, the weight ratio of quinone methide derivative to phenolic compound will generally range from about 90:10 to about 10:90. Most preferred is a weight ratio of about 70:30.

The compositions of the present invention can be introduced into the vinyl aromatic monomer by any conventional method at any point of the processing system, either as separate and individual ingredients or as a combination of ingredients.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer to be treated may be employed. It is often desirable to dissolve the inhibitors in the monomer to which the inhibitor is being added to avoid introducing additional impurities in the monomer. Exemplary liquid carriers include non-polar organic solvents, such as heavy aromatic naphtha and xylene.

The method of the present invention can control the fouling of processing equipment, such as the equipment used in separation and purification processes of styrene monomer, which is due to or caused by the polymerization of the monomer. The instant invention may be used as both a process inhibitor, which is employed during preparation and processing (e.g., employing heat) of the styrene monomer (i.e., ethylbenzene), and as a product inhibitor, which is combined with the styrene monomer in order to inhibit polymerization during storage and handling.

The invention will now be described in conjunction with the following examples which should be viewed as being illustrative of the invention and should not be deemed to limit the invention in any manner.

EXAMPLES

The effect of a combined treatment of QM (Quinone Methide) and 2,6-di-tert butyl phenol on the thermal polymerization of styrene at 115-120° C. was evaluated by comparing polymer formation utilizing the following procedure.

A 250 ml RB flask-equipped with an Ar gas inlet, water cooled condenser and sample outlet was charged with 110 ml of styrene and the candidate polymerization inhibitor(s). [600 ppm (w/v)]. The flask was purged with Argon for 10 minutes. The flask was then immersed into an oil-bath thermostatically controlled at 115-120° C. and heated with purging Ar continuously. Once the temperature reached 115° C., the stop clock was started and this time was considered as time zero. About 5 ml of the sample was removed from the flask at varying time intervals for up to 4 hours and measured precisely before pouring into about 40 ml methanol to precipitate out the styrene polymer. The precipitated polystyrene was filtered with a gas membrane filter that was pre-weighed before use. The polymer was dried at 100° C. and weighed.

Styrene Polymerization Results are Shown in Table I.

TABLE I

Amount of polystyrene formation at 115-120° C. as a function of time for a resultant retarder dosage of about 600 ppm with different ratios of 2,6-tertiary butyl phenol (DTBP) and QM.

| | Polymer wt. in mg | | | | | | |
|---|---|---|---|---|---|---|---|
| Time in minutes | QM (pure) 600 ppm | QM + 2,6-DTBP (569.3 ppm: 31.68 ppm) | QM + 2,6-DTBP (479.98 ppm: 119.07 ppm) | QM + 2,6-DTBP (450.24 ppm: 149.94 ppm) | QM + 2,6-DTBP (420.22 ppm: 180.45 ppm) | QM + 2,6-DTBP (387.3 ppm: 210.78 ppm) | QM + 2,6-DTBP (300.07 ppm: 298.71 ppm) |
| 60 | 19.58 | 15.80 | 12.60 | 10.1 | 6.8 | 13.60 | 16.20 |
| 120 | 42.85 | 34.90 | 24.80 | 23.2 | 15.0 | 29.00 | 34.50 |
| 180 | 70.75 | 59.00 | 41.10 | 40.1 | 26.4 | 50.30 | 58.60 |
| 240 | 105.85 | 89.20 | 60.60 | 60.5 | 40.0 | 76.20 | 90.30 |

TABLE I-continued

Amount of polystyrene formation at 115-120° C. as a function of time for a resultant retarder dosage of about 600 ppm with different ratios of 2,6-tertiary butyl phenol (DTBP) and QM.

| | Polymer wt. in mg | | | | | | |
|---|---|---|---|---|---|---|---|
| Time in minutes | QM (pure) 600 ppm | QM + 2,6-DTBP (569.3 ppm: 31.68 ppm) | QM + 2,6-DTBP (479.98 ppm: 119.07 ppm) | QM + 2,6-DTBP (450.24 ppm: 149.94 ppm) | QM + 2,6-DTBP (420.22 ppm: 180.45 ppm) | QM + 2,6-DTBP (387.3 ppm: 210.78 ppm) | QM + 2,6-DTBP (300.07 ppm: 298.71 ppm) |
| QM (%) | 100.00 | 94.73 | 80.12 | 75.02 | 69.96 | 64.76 | 50.11 |
| 2,6-DTBP (%) | 0.00 | 5.27 | 19.88 | 24.98 | 30.04 | 35.24 | 49.89 |

While we have shown and described herein certain embodiments of the invention, it is intended that these be covered as well as any change or modification therein which may be made without departing from the spirit and scope of the invention as defined in the appended claims.

What is claimed is:

1. A method for inhibiting the polymerization of vinyl aromatic monomer comprising adding to said monomer an effective polymerization inhibiting amount of a compound comprising (A) a quinone methide derivative having the formula

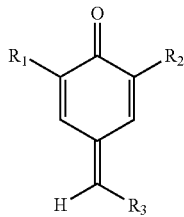

wherein:
R$_1$ and R$_2$ are independently H, C$_4$ to C$_{18}$ alkyl; C$_5$ to C$_{12}$ cycloaklyl; or C$_7$ to C$_{15}$ phenylalkyl, and
R$_3$ is aryl, or aryl substituted with C$_1$ to C$_6$ alkyl, alkoxy, hydroxy, nitro, amino, carboxy, or mixtures thereof; and
(B) a phenol compound having the formula

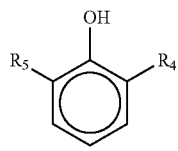

wherein R$_4$ and R$_5$ may be the same or different and are chosen from C$_1$-C$_{20}$ alkyl, C$_1$-C$_{30}$ alkaryl and substituted C$_1$-C$_{30}$ alkaryl.

2. The method as recited in claim 1 wherein the weight ratio of A to B is about 90:10 to about 10:90.

3. The method as recited in claim 2 wherein said quinone methide derivative A) is 2,6-di-tert-butyl-4-benzylidene-cyclohexa-2,5-dienone.

4. The method as recited in claim 3 wherein said phenol compound B) is 2,6-di-tert-butyl phenol.

5. The method as recited in claim 4 wherein from about 1-10,000 ppm of A and B collectively is brought into contact with said vinyl aromatic monomer, based on 1 million parts of said vinyl aromatic monomer.

6. The method as recited in claim 5 wherein said vinyl aromatic monomer comprises styrene monomer.

7. The method as recited in claim 5 wherein the weight ratio of A:B is about 70:30.

8. The method as recited in claim 7 further comprising the step of heating said styrene monomer.

9. The method as recited in claim 7 further comprising the step of distilling said styrene monomer to remove impurities therefrom.

10. Vinyl aromatic monomer anti-polymerization composition comprising a liquid carrier and dissolved or dispersed therein (A) a quinone methide derivative having the formula wherein:
R$_1$ and R$_2$ are independently H, C$_4$ to C$_{18}$ alkyl; C$_5$ to C$_{12}$ cycloaklyl; or C$_7$ to C$_{15}$ phenylalkyl, and
R$_3$ is aryl, or aryl substituted with C$_1$ to C$_6$ alkyl, alkoxy, hydroxy, nitro, amino, carboxy, or mixtures thereof; and
(B) a phenol compound having the formula
wherein R$_4$ and R$_5$ may be the same or different and are chosen from C$_1$-C$_{20}$ alkyl, C$_1$-C$_{30}$ alkaryl and substituted C$_1$-C$_{30}$ alkaryl.

11. Vinyl aromatic monomer anti-polymerization composition as recited in claim 10 wherein A) and B) are present in a weight ratio of about 90:10 to about 10:90.

12. Vinyl aromatic monomer anti-polymerization composition as recited in claim 11 wherein said quinone methide derivative A) is 2,6-di-tert-butyl-4-benzylidene-cyclohexa-2,5-dienone.

13. Vinyl aromatic monomer anti-polymerization composition as recited in claim 12 wherein said phenol compound B) is 2,6-di-tert-butyl phenol.

14. Vinyl aromatic monomer anti-polymerization composition as recited in claim 12 wherein said liquid carrier comprises a non-polar organic solvent and wherein A) and B) are both dissolved in said solvent.

15. Vinyl aromatic monomer anti-polymerization composition as recited in claim 14 wherein said non-polar organic solvent comprises heavy aromatic naphtha or xylene.

16. Vinyl aromatic monomer anti-polymerization composition as recited in claim 10 further comprising styrene monomer.

* * * * *

UNITED STATES PATENT AND TRADEMARK OFFICE
CERTIFICATE OF CORRECTION

PATENT NO.        : 8,298,440 B2
APPLICATION NO.   : 12/793226
DATED             : October 30, 2012
INVENTOR(S)       : Vinod Kumar Rai et al.

It is certified that error appears in the above-identified patent and that said Letters Patent is hereby corrected as shown below:

In the Claims

In Claim 10, column 6, line 32, after ...having the formula..., please insert

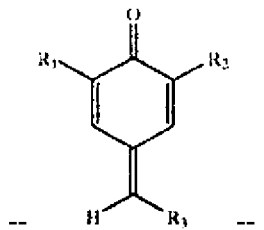

In Claim 10, column 6, line 36, after ...having the formula..., please insert

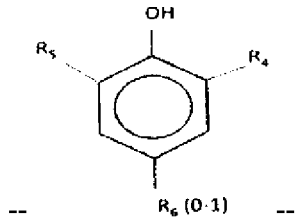

Signed and Sealed this
Fifteenth Day of January, 2013

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,298,440 B2 |
| APPLICATION NO. | : 12/793226 |
| DATED | : October 30, 2012 |
| INVENTOR(S) | : Vinod Kumar Rai et al. |

It is certified that error appears in the above-identified patent and that said Letters Patent is hereby corrected as shown below:

In the Claims

In Claim 10, column 6, line 32, after ...having the formula..., please insert

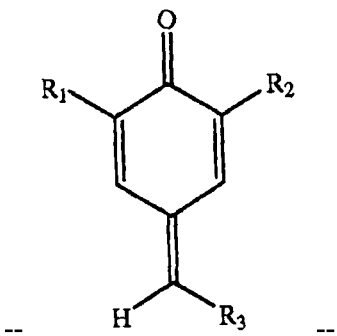

In Claim 10, column 6, line 36, after ...having the formula..., please insert

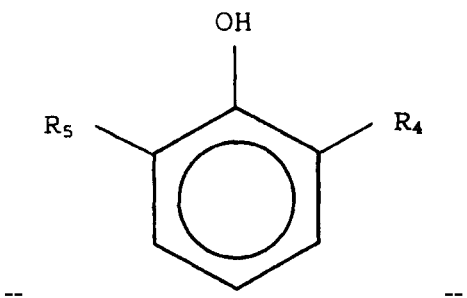

This certificate supersedes the Certificate of Correction issued January 15, 2013.

Signed and Sealed this
Sixteenth Day of July, 2013

Teresa Stanek Rea
*Acting Director of the United States Patent and Trademark Office*